US008070686B2

(12) United States Patent
Belalcazar et al.

(10) Patent No.: US 8,070,686 B2
(45) Date of Patent: Dec. 6, 2011

(54) MONITORING LUNG FLUID STATUS USING THE CARDIAC COMPONENT OF A THORACIC IMPEDANCE-INDICATING SIGNAL (75) Inventors: Andres Belalcazar, St. Paul, MN (US); Aaron Lewicke, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 349 days.

(21) Appl. No.: 11/772,352

(22) Filed: Jul. 2, 2007

(65) Prior Publication Data
US 2009/0012416 A1    Jan. 8, 2009

(51) Int. Cl.
A61B 5/08    (2006.01)
(52) U.S. Cl. ........................................ 600/529; 600/547
(58) Field of Classification Search .................. 600/536, 600/509, 504–507, 483, 484
See application file for complete search history.

(56) References Cited

U.S. PATENT DOCUMENTS

| | | | |
|---|---|---|---|
| 3,815,611 A | | 6/1974 | Denniston, III |
| 3,851,641 A | * | 12/1974 | Toole et al. .................. 600/529 |
| 4,587,975 A | | 5/1986 | Salo et al. |
| 5,003,976 A | * | 4/1991 | Alt ................................ 607/18 |
| 5,417,717 A | | 5/1995 | Salo et al. |
| 5,957,861 A | | 9/1999 | Combs et al. |
| 6,278,894 B1 | | 8/2001 | Salo et al. |
| 6,360,123 B1 | * | 3/2002 | Kimchi et al. ................ 600/547 |
| 6,406,421 B1 | | 6/2002 | Grandjean et al. |
| 6,449,509 B1 | | 9/2002 | Park |
| 6,473,640 B1 | | 10/2002 | Erlebacher |
| 6,788,970 B1 | | 9/2004 | Park et al. |
| 2003/0109790 A1 | * | 6/2003 | Stickney et al. .............. 600/500 |
| 2004/0102712 A1 | * | 5/2004 | Belalcazar et al. ........... 600/547 |
| 2004/0116819 A1 | | 6/2004 | Alt |

(Continued)

FOREIGN PATENT DOCUMENTS
WO    WO-2004/047638 A1    6/2004
(Continued)

OTHER PUBLICATIONS

Belalcazar, Andres, "Monitoring Fluid in a Subject Using a Weight Scale", U.S. Appl. No. 11/419,120, filed May 18, 2006, 43 Pages.
(Continued)

Primary Examiner — Patricia Mallari
Assistant Examiner — Michael D'Angelo
(74) Attorney, Agent, or Firm — Schwegman, Lundberg & Woessner, P.A.

(57) ABSTRACT

This patent document describes, among other things, systems and methods for monitoring lung fluid status, such as monitoring the presence or absence of pulmonary edema, in a subject using information about the cardiac impedance-indicating component of a measured impedance-indicating signal. In various examples, an amplitude or contribution change over multiple cardiac cycles of the cardiac impedance-indicating component is used to compute and provide a lung status indication. In various examples, a decreasing amplitude or contribution trend of the cardiac impedance-indicating component signifies an increasing amount of fluid in the subject's lungs, as a greater portion of an injected thoracic impedance measurement current formerly traversing the heart is rerouted through the lung due to the less resistance path created by the fluid accumulation therein. In another example, measurements of the impedance-indicating signal, and thus the cardiac impedance-indicating component, are taken at one or a combination of end-inspiration or end-expiration.

26 Claims, 7 Drawing Sheets

U.S. PATENT DOCUMENTS

| | | |
|---|---|---|
| 2004/0220628 A1 | 11/2004 | Wagner |
| 2005/0004610 A1 | 1/2005 | Kim et al. |
| 2006/0041280 A1 | 2/2006 | Stahmann et al. |
| 2006/0184060 A1 | 8/2006 | Belalcazar et al. |
| 2006/0241513 A1 | 10/2006 | Hatlestad et al. |
| 2006/0264776 A1 | 11/2006 | Stahmann et al. |
| 2007/0270707 A1 | 11/2007 | Belalcazar |

FOREIGN PATENT DOCUMENTS

| | | |
|---|---|---|
| WO | WO-2004/101062 A2 | 11/2004 |

OTHER PUBLICATIONS

"International Application Serial No. PCT/US2008/004914, International Search Report mailed Aug. 27, 2008", 4 pgs.

"International Application Serial No. PCT/US2008/004914, Written Opinion mailed Aug. 27, 2008", 12 pgs.

Lichtwarck-Aschoff, M. L., et al., "Decreasing size of cardiogenic oscillations reflects decreasing compliance of respiratory system during long-term ventilation", *Journal of Applied Physiology,* .96, (2004), 879-884.

Madias, J. E., et al., "Relationship Among Electrocardiographic Potential Amplitude, Weight and Resistance/Reactance/Impedance in a Patient With Peripheral Edema Treated for Congestive Heart Failure", *Journal of Electrocardiology,* 36, (2003), 167-171.

"European Application No. 08779584.5, Office Action mailed Jul. 21, 2010", 4 pgs.

"Australian Application Serial No. 2008271262, Request to Amend filed Jan. 5, 2011 to First Examiner Report mailed Oct. 19, 2010", 7 pgs.

"Australian Application Serial No. 2008271262, First Examiner Report mailed Oct. 19, 2010", 4 pgs.

"Australian Patent Application Serial No. 2008271262, Second Statement of Proposed Amendments filed Jan. 7, 2011", 17 pgs.

"European Application Serial No. 08779584.5, Response filed Dec. 15, 2010 to Communication dated Jul. 21, 2010", 17 pgs.

\* cited by examiner

MONITORING LUNG FLUID STATUS USING THE CARDIAC COMPONENT OF A THORACIC IMPEDANCE-INDICATING SIGNAL

TECHNICAL FIELD

This patent document pertains generally to medical systems and methods. More particularly, but not by way of limitation, this patent document pertains to medical systems and methods configured for monitoring lung fluid status using information about the cardiac component of a measured thoracic impedance-indicating signal.

BACKGROUND

Excess thoracic fluid retention can take various forms and can have different causes. As an example, thoracic fluid accumulation may result from pulmonary edema, which involves a build-up of extravascular fluid in or around a subject's lungs.

One cause of pulmonary edema is congestive heart failure ("CHF"), sometimes referred to simply as "heart failure." CHF can be conceptualized as an enlarged weakened heart muscle. The impaired heart muscle results in poor cardiac output of blood. Consequently, blood tends to pool in blood vessels in the lungs and affects normal oxygen exchange. For this reason, pulmonary edema can be an indicator of CHF.

Pulmonary edema can present a medical emergency that requires immediate care. However, the outlook for pulmonary edema patients can be good if detected early and treated promptly. If left undetected, and consequently untreated, pulmonary edema can lead to death.

OVERVIEW

The present inventors have recognized, among other things, that one problem presented by heart failure is its timely detection and treatment. The present inventors have further recognized that there exists an unmet need for enhanced, yet simple monitoring of excess fluid accumulation in the thoracic region of a subject, such as the subject's lungs.

This patent document describes, among other things, systems and methods for monitoring lung fluid status, such as monitoring the presence or absence of pulmonary edema, in a subject using information about the cardiac impedance-indicating component of a measured impedance-indicating signal. In various examples, an amplitude or contribution change over multiple cardiac cycles of the cardiac impedance-indicating component is used to compute and provide a lung status indication. In various examples, a decreasing amplitude or contribution trend of the cardiac impedance-indicating component signifies an increasing amount of fluid in the subject's lungs, as a greater portion of an injected thoracic impedance measurement current formerly traversing the heart is rerouted through the lung due to the less resistance path created by the fluid accumulation therein. In another example, measurements of the impedance-indicating signal, and thus the cardiac impedance-indicating component, are taken at one or a combination of end-inspiration or end-expiration.

In Example 1, a system comprises an implantable medical device including an electrical impedance measurement circuit configured for injecting electrical energy between two or more electrodes and for concurrently measuring a potential difference created thereby in a thoracic region of a subject between the same or different two or more electrodes; and an implantable or external processor circuit including an input to receive the information about the injected electrical energy and the measured potential difference, the processor circuit configured to compute an impedance-indicating signal using the information about the electrical energy and the potential difference, the processor circuit further configured to determine an amplitude change over time of a cardiac impedance-indicating component of the impedance-indicating signal to provide a lung fluid status indication.

In Example 2, the system of Example 1 optionally comprises a comparator circuit configured to compare an amplitude of a first cardiac impedance-indicating component to an amplitude of a second cardiac impedance-indicating component; and the processor circuit is configured to use information about the comparison to provide the lung fluid status indication.

In Example 3, the system of Examples 1-2 optionally comprises a comparator circuit configured to compare the amplitude change over time of the cardiac impedance-indicating component to a specified threshold; and the processor circuit is configured to use information about the comparison to provide the lung fluid status indication.

In Example 4, the system of Examples 1-3 optionally comprises a contribution circuit configured to compute a contribution coefficient of the cardiac impedance-indicating component to the impedance-indicating signal; and the processor circuit is configured to use information about the contribution coefficient to provide the lung fluid status indication.

In Example 5, the system of Examples 1-4 optionally comprises a memory circuit configured to store information about the amplitude change over time of the cardiac impedance-indicating component, the time association with the amplitude change exceeding a respiration cycle length time.

In Example 6, the system of Examples 1-5 optionally comprises a regimen control circuit configured to initiate or adjust a regimen provided to the subject using, at least in part, information about at least one of the amplitude change over time of the cardiac impedance-indicating component or the lung fluid status indication.

In Example 7, the system of Examples 1-6 optionally comprises an external user-interface device communicatively coupled to the implantable medical device and including a user-detectable indication of at least one of the change over time of the cardiac impedance-indicating component or the lung fluid status indication.

In Example 8, the system of Example 7 is optionally configured such that the external user-interface device includes a user input device configured to receive programming information from a user and to communicate the programming information to the implantable medical device.

In Example 9, the system of Examples 1-8 optionally comprises a respiration sensor configured to produce a respiration signal indicative of a moment of one or a combination of end-inspiration or end-expiration; and the electrical impedance measurement circuit is configured to measure the impedance-indicating signal at the respiration signal.

In Example 10, the system of Examples 1-9 optionally comprises a posture sensor circuit configured to produce a posture signal indicative of a posture of a subject; and the electrical impedance measurement circuit is configured to measure the impedance-indicating signal at a specified posture signal.

In Example 11, a method comprises measuring an impedance-indicating signal indicative of an impedance of a thoracic region of a subject between at least two electrodes; extracting amplitude contribution information about a cardiac impedance-indicating component from the impedance-indicating signal; and computing a lung fluid status indication using, at least in part, the extracted amplitude contribution information about the cardiac impedance-indicating component.

In Example 12, the method of Example 11 is optionally configured such that measuring the impedance-indicating signal includes injecting electrical energy between a first and a second electrode implanted in the thoracic region of the subject; and measuring a potential difference between a third and a fourth electrode implanted in the thoracic region of the subject, the potential difference resulting from the electrical energy injected between the first and second electrodes.

In Example 13, the method of Example 12 optionally comprises determining an amount of the injected electrical energy which traverses a heart of the subject using the extracted amplitude contribution information about the cardiac impedance-indicating component; and computing the lung fluid status indication includes using the amount of the injected electrical energy which traverses the heart.

In Example 14, the method of Example 12 optionally comprises determining an approximate amount of the injected electrical energy which traverses a lung of the subject using the extracted amplitude contribution information about the cardiac impedance-indicating component; and computing the lung fluid status indication includes using the amount of the injected electrical energy which traverses the lung.

In Example 15, the method of Example 12 is optionally configured such that injecting the electrical energy includes injecting an electrical current between an electrode disposed on a left ventricular lead and one of a housing or a header electrode of an implantable medical device; and measuring the potential difference includes detecting a voltage potential between an electrode disposed on the left ventricular lead and one of the housing or the header electrode.

In Example 16, the method of Examples 11-15 optionally comprises comparing an amplitude of a first cardiac impedance-indicating component and an amplitude of a second cardiac impedance-indicating component, including determining an amplitude change over a period of time exceeding a respiration cycle length time of the cardiac impedance-indicating component.

In Example 17, the method of Example 16 optionally comprises comparing the change over the period of time of the cardiac impedance-indicating component to a specified threshold.

In Example 18, the method of Examples 11-17 optionally comprises positioning at least one of the two or more electrodes near the interface between a heart and a lung of the subject.

In Example 19, the method of Examples 11-18 optionally comprises attenuating one or a combination of a posture effect, a blood resistivity effect, a physical activity state effect, or a cardiac effect from at least one of the impedance-indicating signal or the cardiac impedance-indicating component.

In Example 20, the method of Examples 11-19 optionally comprises initiating or adjusting a regimen in response to the computed lung fluid status indication.

In Example 21, the method of Examples 11-20 optionally comprises measuring the impedance-indicating signal at a first injection electrical energy frequency and measuring the impedance-indicating signal at a second injection electrical energy frequency different from the first injection electrical energy frequency; and determining a level of confidence in the computed lung fluid status indication using cardiac impedance-indicating component information extracted from the impedance-indicating signals measured at the first and second injection frequencies.

In Example 22, the method of Examples 11-21 optionally comprises computing a lung tidal volume status indication using, at least in part, the extracted amplitude contribution information about the cardiac impedance-indicating component.

In Example 23, the method of Examples 11-22 is optionally configured such that measuring the impedance-indicating signal includes measuring the impedance at one or a combination of end-inspiration or end-expiration.

In Example 24, the method of Examples 11-23 is optionally configured such that extracting the amplitude contribution information includes calculating a ratio of the cardiac impedance-indicating component to the impedance-indicating signal.

In Example 25, the method of Examples 11-24 is optionally configured such that computing the lung fluid status indication includes detecting a decrease in the amplitude contribution of the cardiac impedance-indicating component over time.

In Example 26, the method of Examples 11-25 is optionally configured such that computing the lung fluid status indication includes determining the presence or absence of pulmonary edema.

Advantageously, the present fluid monitoring systems and methods can be designed for use with existing implantable medical devices, such as upon firmware or programming modifications of the existing devices, thereby resulting in cost savings. In addition, the present systems and methods may provide for enhanced monitoring of excess fluid accumulation in a subject's thoracic region and thus, may provide a more timely or accurate detection of thoracic fluid accumulation than is currently available. Such detection is made possible by, among other things, generating a measured thoracic impedance-indicating signal and extracting from this signal, information about the cardiac impedance-indicating component, such as the cardiac component's amplitude or contribution (to the total measured thoracic impedance) trend over multiple cardiac cycles. Once extracted and optionally trended, this cardiac impedance-indicating component information can be used to determine a lung fluid status, such as an indication of present or impending lung fluid accumulation.

Unlike previous fluid monitoring systems and methods, determining the indication of present or impending lung fluid accumulation using the present systems and methods does not depend on a highly-filtered, low frequency direct current (DC) or near-DC component of a thoracic impedance-indicating signal. Rather, the indication of present or impending lung fluid accumulation can be found, at least in some examples, through the use of a thoracic impedance-indicating signal including higher frequency alternating current (AC) components thereby providing simpler monitoring, which may be less costly to implement.

These and other examples, advantages, and features of the present lung fluid monitoring systems and methods will be set forth in part in the following Detailed Description. As such, this Overview is intended to provide an overview of subject matter of the present patent document. It is not intended to provide an exclusive or exhaustive explanation of the invention. The Detailed Description is included to provide further information about the present patent document.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

In general, an excess fluid accumulation in a region of a subject, typically referred to simply as "edema," can be conceptualized as a failure or decompensation of one or more homeostatic processes within the subject's body. The body normally prevents the accumulation of fluids therewithin by maintaining adequate pressures and concentrations of salts and proteins, and by actively removing excess fluid. If a disease affects any of these normal bodily mechanisms or if the normal bodily mechanisms are unable to keep up with the fluid accumulation, the result can be edema, such as pulmonary edema.

Figure 1:
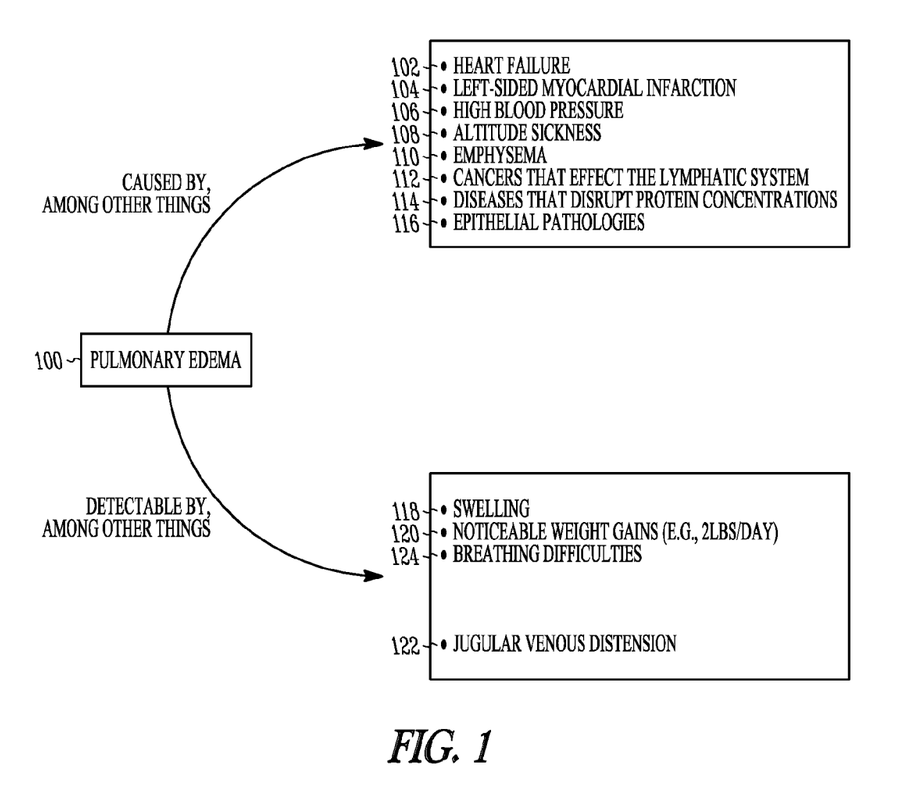
FIG. 1 is a block diagram illustrating various causes and indications of pulmonary edema in a subject.

There are several conditions or diseases that can cause or affect pulmonary edema. As shown in FIG. 1, this includes, among others, heart failure 102, left-sided myocardial infarction 104, high blood pressure 106, altitude sickness 108, emphysema 110, cancers that affect the lymphatic system 112, diseases that disrupt protein concentrations 114, or epithelial pathologies 116, such as those caused by inhalation of toxic chemicals, leading to flooding of the alveoli. While pulmonary edema 100 can be a sign of many conditions or diseases, the prospect that pulmonary edema 100 can be a sign of failing heart 102 circulation is often of first concern to caregivers (e.g., health care professionals) due to the severity of its nature.

Unfortunately, the first indication that an attending caregiver typically has of an occurrence of pulmonary edema 100 is very late in the disease process, such as when it becomes physically manifested by swelling 118, noticeable weight gain 120, jugular venous distension 122, or breathing difficulties 124 that are so overwhelming as to be noticed by the subject, who then proceeds to be examined by his or her caregiver. For a heart failure subject, hospitalization at such a physically apparent time will likely be required.

In an effort to timely and accurately detect impending edema, such as pulmonary edema, and avoid its associated hospitalizations, the present ambulatory fluid monitoring systems and methods use the cardiac impedance-indicating component of a measured thoracic impedance-indicating signal. By looking at one or both of amplitude or contribution (to the total measured thoracic impedance) trends of the cardiac impedance-indicating component, an indication of present or impending lung fluid accumulation can be computed and provided.

The present fluid monitoring systems and methods are based on a number of recognitions made by the present inventors. As one example, the present inventors have found that when a lung is more electrically conductive, such as when it has more fluid or less air in it, a greater portion of an injected current or other electrical energy used to initiate a thoracic impedance measurement will pass through the lung due to the less resistance path created by the fluid accumulation, and less of the injected energy will pass through the heart and venous system. As a result of less injection energy passing through the heart and venous system, the cardiac indicating component of the thoracic impedance-indicating signal will be smaller in one or both of amplitude or contribution to the overall thoracic impedance measurement amplitude. Conversely, if a lung has less fluid and is therefore less electrically conductive, a greater portion of the injected energy will pass through the heart and venous system resulting in a larger cardiac indicating component amplitude and/or contribution. Accordingly, it is believed that by monitoring changes in one or both of amplitude or contribution level of the cardiac impedance-indicating component, and thus indirectly monitoring a path traversed by the injected current or energy, a lung fluid status indication may be computed and provided.

Figure 2:
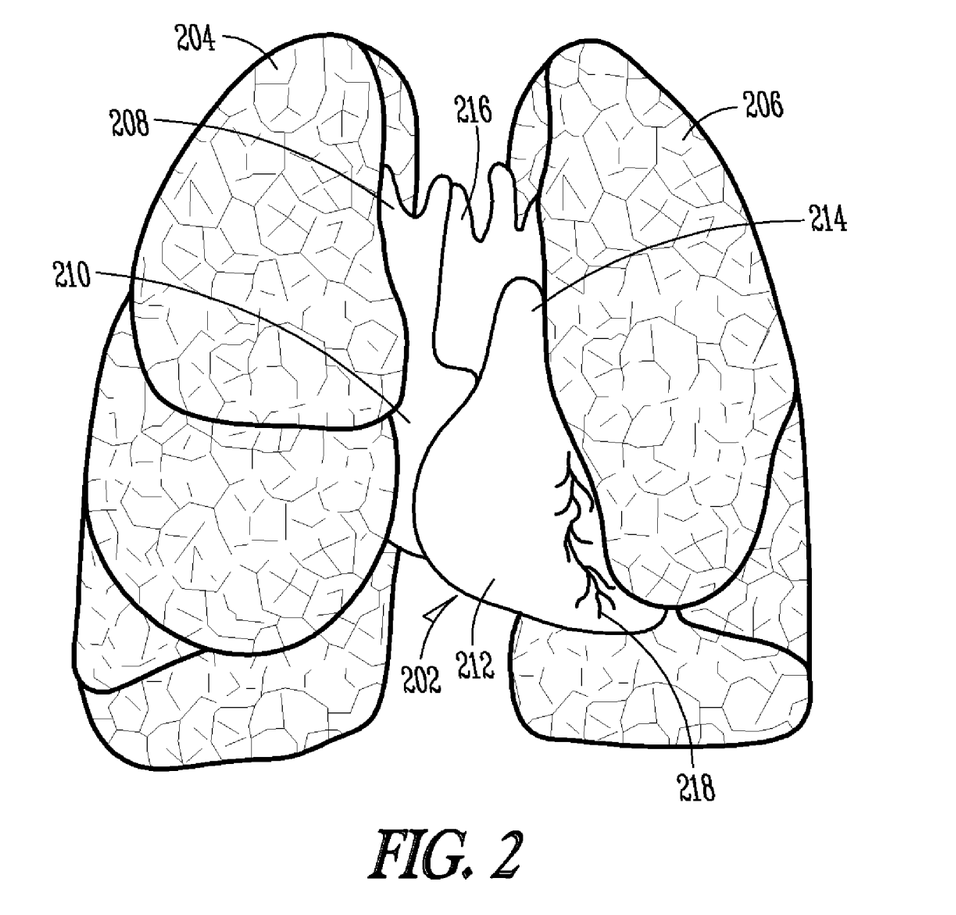
FIG. 2 is a schematic view of a subject's heart and lungs and relative positioning between the same.

FIG. 2 is a front view of a heart 202 positioned between a right lung 204 and a left lung 206. A superior vena cava 208 receives deoxygenated blood from a subject's upper extremities and thorax, and empties the blood into a right atrial chamber 210, which is commonly referred to as the "right atrium." A left atrial chamber receives oxygenated blood from the lungs 204, 206. The atria (i.e., the right atrium 210 and the left atrium) then contract and force blood into a right ventricular chamber 212, which is commonly referred to as the "right ventricle," and a left ventricular chamber, which is commonly referred to as the "left ventricle," covered by the left lung 206, respectively. After this atrial contraction, the cardiac cycle reaches the end of diastole, with the ventricles dilated and filled with blood. The right ventricle 212 and the left ventricle serve as blood pumps to pump blood away from the heart 202. The right ventricle 212 pumps deoxygenated blood to the lungs 204, 206 through a pulmonary artery 214. Within the lungs 204, 206, the blood becomes re-oxygenated and is then moved to the left atrium, as discussed above. The left ventricle, having received oxygenated blood from the lungs 204, 206 through the left atrium, pumps the oxygenated blood to the body through an aorta 216, a large artery leaving the left ventricle.

In FIG. 2, a section of the aorta 216 known as the aortic arch is shown. An inter-ventricular vein 218, which is illustrated as extending substantially vertically, marks a division between the right ventricle 212 and the left ventricle. As shown in FIG. 2, the lungs 204, 206 are in close proximity to the heart 202, the closest portions being the left ventricle and the right atrium 210. The right ventricle, in contrast, is located away from the lungs 204, 206, approximately between the right lung 204 and the left lung 206 on the anterior side.

Figure 3A:
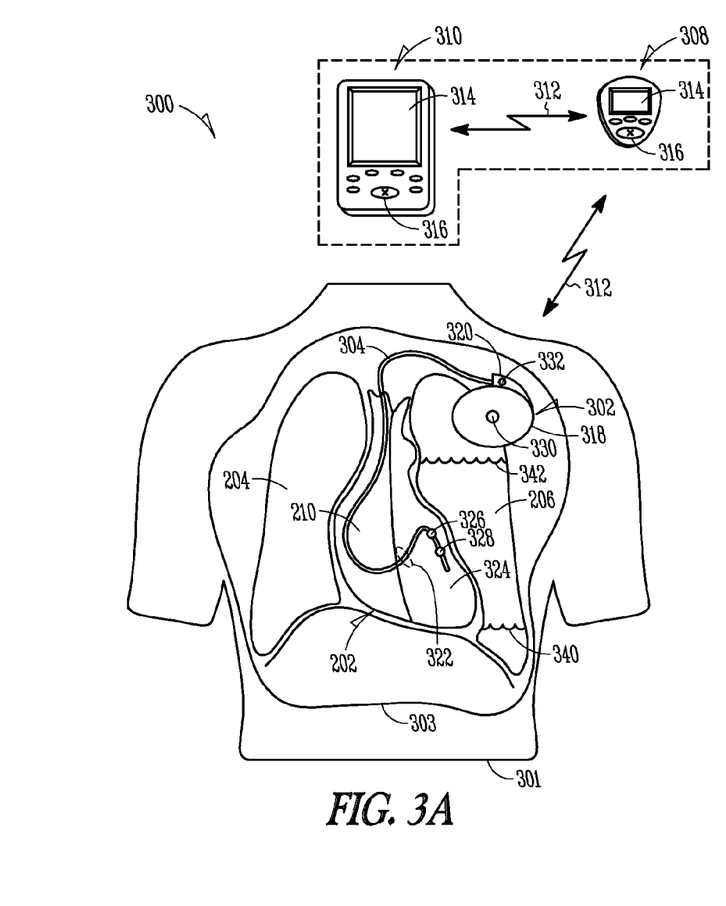
FIGS. 3A-3B are schematic views illustrating various conceptual examples of systems configured for monitoring excess fluid accumulation in a subject's lungs using one or both of amplitude or contribution information about the cardiac impedance-indicating component of a measured thoracic impedance-indicating signal, and an environment in which the system can be used.
Figure 3B:
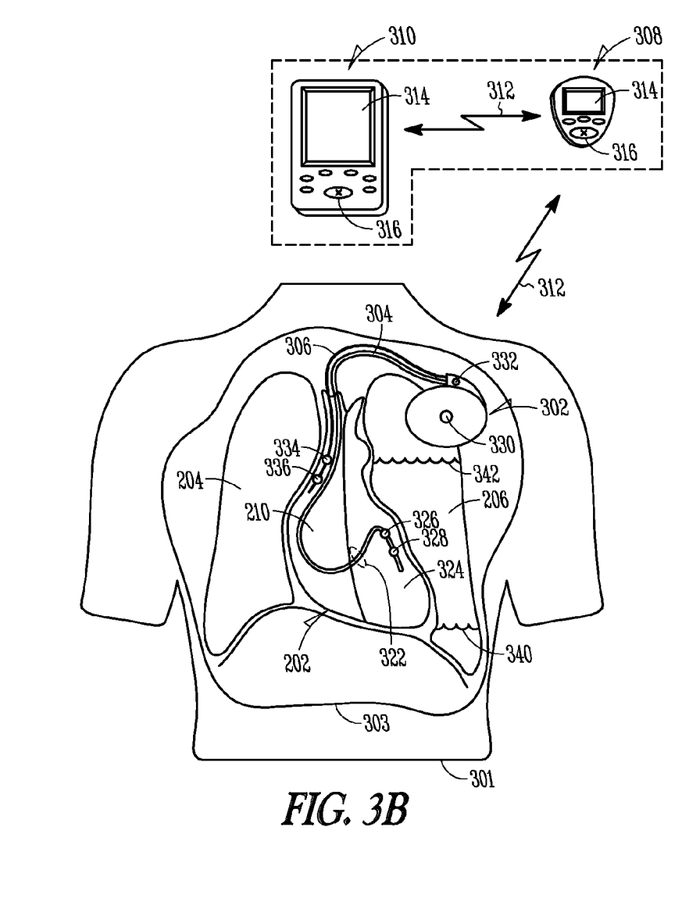

FIGS. 3A-3B show a heart 202 and lungs 204, 206 of a subject 301 (via a cut-away portion 303) and a system 300 configured for monitoring excess fluid accumulation in the lungs, such as the left lung 206, using one or both of amplitude or contribution information about the cardiac impedance-indicating component of a measured thoracic impedance-indicating signal. In FIGS. 3A-3B, the system 300 includes a pectorally-implanted IMD 302, such as a CRM device, which is coupled via one or more electrode-bearing cardiac leads 304, 306 to the heart 202 of the subject 301. The system 300 also includes one or more programmers or other external user-interface devices 308 (nearby), 310 (distant) providing wireless communication with the IMD 302, such as by using telemetry 312 or another communication technique. As shown, the external user-interface devices 308, 310 can include, among other things, a user-detectable indication 314, such as an LCD or LED display, for textually or graphically relaying information about at least one of the measured thoracic impedance-indicating signal, the cardiac impedance-indicating component of the impedance-indicating signal, or a computed lung fluid status indication to the subject 301 or his or her caregiver. The external user-interface devices 308, 310 can include a user input device 316 configured for receiving programming information from a user and communicating the programming information to the IMD 302.

In FIG. 3A, the IMD 302 includes a housing 318 that houses an electrical impedance measurement circuit configured for measuring the thoracic impedance-indicating signal. The IMD 302 can include a left ventricular port in a header 320 thereof for receiving a proximal end of an electrode-bearing left ventricular lead 304. A distal end of the left ventricular lead 304 can be introduced into the venous system, down the superior vena cava 208 (FIG. 2), into the right atrium 210, into a coronary sinus through an orifice 322, and then further into a coronary vein, which runs epicardially over the left ventricle 324.

In the example shown, the left ventricular lead 304 includes two electrodes 326, 328 that are electrically connected to respective conductors that run through the lead 304. The conductors connect to conducting wires within the IMD 302 when the left ventricular lead 304 is received by the left ventricular lead port, thereby establishing electrical connections between the electrical impedance measurement circuit and the electrodes 326, 328. In this example, the electrode 326 can be referred to as a left ventricular proximal electrode, while electrode 328 can be referred to as a left ventricular distal electrode, due to their relative positions on the left ventricular lead 304. While the left ventricular lead 304 shown in FIG. 3A is bipolar in nature, the lead 304 can optionally include additional or fewer electrodes, and can further follow a different path through the heart 202 from that shown and described.

A housing electrode 330 on an exterior surface of the IMD housing 318 can be electrically connected to the electrical impedance measurement circuit to complete a tripolar electrode configuration in which electrical energy (e.g., current) is injected between a lead electrode, such as the left ventricular distal electrode 328, and the housing electrode 330, and a potential difference (i.e., a voltage) created by the injected energy can be measured between the other lead electrode—in this example, the left ventricular proximal electrode 326—and the housing electrode 330. The IMD 302 can optionally include a second housing or header electrode 332 to facilitate a tetrapolar electrode configuration whereby electrical energy is injected, for example, between a the left ventricular distal electrode 328 and the housing electrode 330, and a responsive potential difference created by the energy is measured between the left ventricular proximal electrode 326 and the header electrode 332.

In FIG. 3B, the IMD 302 includes not only a left ventricular port in the header 320 thereof for receiving the proximal end of the left ventricular lead 304, but also includes a right atrial port for receiving a proximal end of an electrode-bearing right atrial lead 306. A distal end of the right atrial lead 306 is shown in this example as being introduced into the venous system, down the superior vena cava 208 (FIG. 2), and into the right atrium 210. In the example shown, the right atrial lead 306 includes two electrodes 334, 336 that are electrically connected to conductors that run through the lead 306. The conductors connect to conducting wires within the IMD 302 when the right atrial lead 306 is received by the right atrial lead port, thereby establishing electrical connections between the electrical impedance measurement circuit and the electrodes 334, 336. In this example, the electrode 334 can be referred to as a right atrial proximal electrode, while electrode 336 can be referred to as a right atrial distal electrode, due to their relative positions on the right atrial lead 306. While the right atrial lead 306 shown in FIG. 3B is bipolar in nature, the lead 306 can optionally include additional or fewer electrodes and can follow a different path through the heart 202 from that shown and described.

The addition of the right atrial lead 306 in FIG. 3B provides a tetrapolar electrode configuration for measuring thoracic impedance-indicating signals whereby electrical energy is injected, for example, between the housing electrode 330 and the left ventricular distal electrode, and a potential difference created by the energy is measured between the left ventricular proximal electrode one of the right atrial proximal electrode 334 or the right atrial distal electrode 336. In this example, should the left ventricular lead 304 not be available, thoracic impedance-indicating signals can be measured by injecting electrical energy between the housing electrode 330 and the right atrial distal electrode 336, and a potential difference created by the energy can be measured between the housing electrode 330 or the header electrode 332 and the right atrial proximal electrode 334.

Because the human body includes a number of thoracic organs, tissues, and fluids, measurement of thoracic impedance can include contributions from each of the various organs, tissues, and fluids. For example, resistivities of the heart muscle, lungs, pectoral muscle, pectoral fat, liver, kidneys, spleen, stomach, skeletal muscle, bone, cartilage, blood and other tissues and fluids each can contribute to a measurement of thoracic impedance. As such, changes in measured thoracic impedance can be caused by changes in the resistivities of these and other organs or tissues.

Thus, when measuring impedance, such as thoracic impedance, to detect or assess one or more pathologies or conditions, such as pulmonary edema, it can be desirable to measure the impedance-indicating signals using electrode configurations that are more sensitive to a particular region or regions of interest. Electrode configurations having greater sensitivity to the region or regions of interest may permit sensitive, enhanced detection of resistivity changes in the organ(s) or tissue(s) of interest, as the change in resistivity of the organ(s) or tissue(s) of interest will have a correspondingly large impact on the measured impedance. In the examples of FIGS. 3A-3B, placement of the left ventricular lead 304 and the right atrial lead 306 near the left ventricle 324 and the right atrium 210 of the heart 202, respectively, provide an example of a suitable location for measuring thoracic impedance, and more specifically heart and lung impedance, due to the proximity of the heart and lungs 204, 206 thereto. Although not shown, a right ventricular lead having right ventricular electrodes or a left ventricular epicardial lead having left ventricular epicardial electrodes can also be used in one or more thoracic impedance measurement configurations.

In various examples, the electrical impedance measurement circuit within the IMD 302 in conjunction with the lead, header, or housing electrodes measure thoracic impedance-indicating signals by injecting a relatively small amplitude electrical energy (e.g., a current) between at least two implanted electrodes and concurrently measuring an responsive induced potential difference between (the same or different) at least two implanted electrodes, such as discussed above. Because the magnitude of the injected electrical energy is typically specified, the measurement of the responsive potential difference allows for a thoracic impedance-indicating signal measurement to be determined from Ohm's law (i.e., impedance-indicating signal=(potential difference)/(injected current)).

Certain system and methods configured for thoracic and other fluid accumulation assessments focus on the lower frequency DC or near-DC components of the measured thoracic impedance-indicating signal, such as by the complex filtering out of the higher frequency AC signal components. Unlike conventionally, highly-filtered systems and methods, the present fluid monitoring systems and methods allow for fluid accumulation assessments to be made without first requiring that the impedance-indicating signal be filtered to its DC or near-DC components. Noteworthy is that the present systems and methods can use the DC or near-DC components in ways similar to those discussed herein to monitor fluid accumulation.

As previously mentioned, the present inventors have found that when a lung 204, 206, for example, is more conductive, such as when its has more fluid or less air in it, a greater portion of the injected electrical energy used in a thoracic impedance measurement will pass through the lung 204, 206 and less of the energy will be influenced by the heart 202 region and pass therethrough. As a result of less injection energy passing through the heart 202 region, the cardiac indicating component of the thoracic impedance-indicating signal will be smaller in one or both of amplitude or contribution to the (overall) thoracic impedance measurement. Conversely, if the lung 204, 206 has less fluid and is therefore less electrically conductive, a greater portion of the injected energy will pass through the heart 202 region resulting in a larger cardiac indicating component amplitude and/or contribution.

Accordingly, by monitoring certain characteristics, such as amplitude or contribution to the total measured thoracic impedance, of the cardiac impedance-indicating component of the impedance-indicating signal during injection of the energy, the system 300 can determine the thoracic path traversed by the injected energy and in so doing, can obtain information about the amount of fluid in the lung 204, 206. In one example, as the fluid level within the left lung 206 increases from a lower level 340 to a higher level 342, a decrease in cardiac impedance-indicating component amplitude is detected, stored, and communicated by the system 300, thereby providing an indication of present or impending lung fluid accumulation, and potentially providing an indication of pulmonary edema. See, e.g., FIG. 4B. Similarly, in another example, as the fluid level within the left lung 206 increases from the lower level 340 to a higher level 342, a decreasing contribution of the cardiac impedance-indicating component to the total measured thoracic impedance can be recognized, stored, and communicated by the system 300 providing an indication of present or impending lung fluid accumulation.

Such cardiac impedance-indicating component information can be used alone, or with other information about fluid accumulation, such as the low-frequency (DC or near-DC) component information of the thoracic impedance signal. In another example, lung tidal volume can be monitored using the cardiac impedance-indicating component techniques discussed herein, as air content (in addition to fluid accumulation) causes the current diversion described above. Such tidal volume information can be used in addition to the cardiac impedance-indicating component information or the low-frequency (DC or near-DC) component of the thoracic impedance signal to provide an indication of lung fluid status.

Figure 4A:
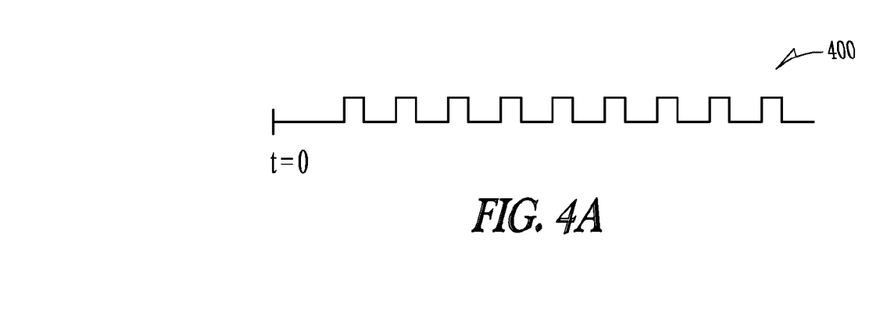
FIG. 4A is a timing diagram illustrating one conceptual example of an injected current or other electrical energy used in a thoracic impedance measurement, the current or energy having a specified magnitude, frequency, and duration.

FIG. 4A is a timing diagram 400 illustrating one conceptual example of a sub-stimulation current or other electrical energy pulse train injected between two implanted electrodes and used to induced a potential difference (i.e., a voltage) between two implanted electrodes. Using information about the injected energy and responsive potential difference in conjunction with Ohm's law, an impedance-indicating signal, such as a thoracic impedance-indicating signal, can be determined. In one example, the injected current or other energy pulse train is an alternating current (AC) to avoid undesirable polarization and electrolytic degradation effects at the electrodes. In addition, the injected current has a magnitude, frequency, and duration that does not cause cardiac stimulation. In one such example, the injected current includes a frequency of about 50 KHz-100 KHz.

Optionally, more than one injection frequency can be used by the present fluid monitoring system 300, such as to enhance the sensitivity (e.g., the ability of a detection scheme to effectively detect that which a user desires to detect or treat) or specificity (e.g., the ability of a detection scheme to avoid erroneous or "false" detections that a user desires to detect or treat) of the measured impedance-indicating signal based on the fact that cardiac muscle and thoracic impedance-indicating signals have different signatures at different injection energy frequencies. Thus, if the cardiac impedance-indicating component amplitude, for example, of the thoracic impedance-indicating signal measured at different injection energy frequencies exhibits similar changes over time, a more confident judgment can be made that the changes are due to fluid accumulation and not to one or more other factors, such as intrinsic properties of cardiac muscle.

Figure 4B:
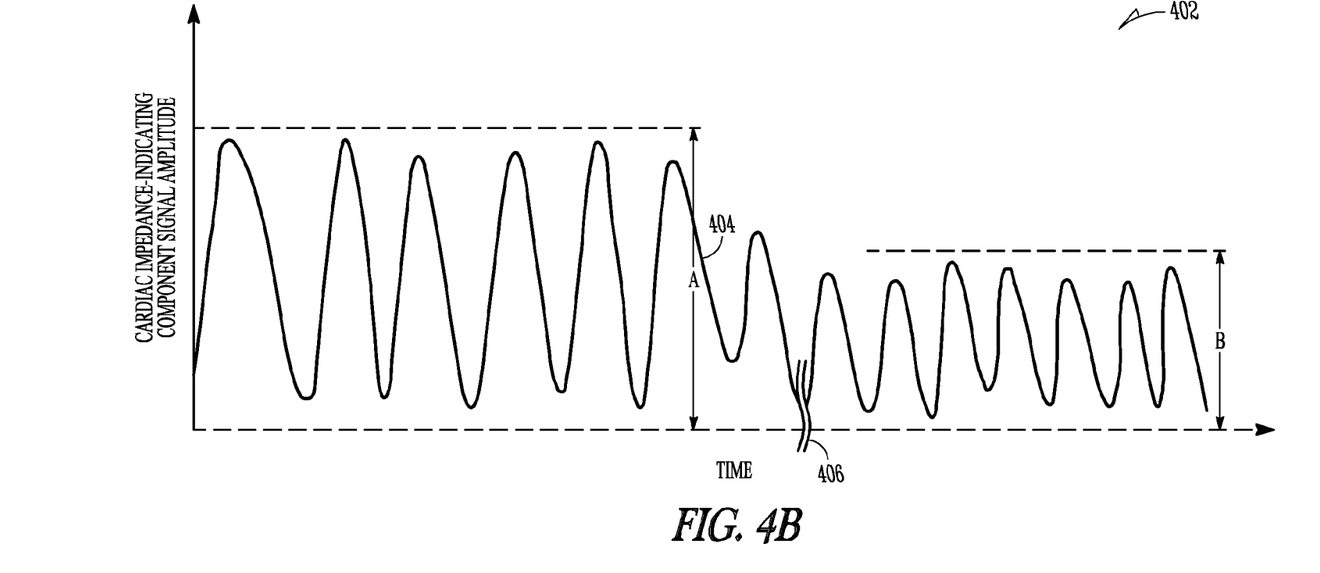
FIG. 4B is a plot illustrating one conceptual example of a signal curve representing a generally decreasing pulsation amplitude over time of the cardiac impedance-indicating component of a measured thoracic impedance-indicating signal, the decreasing amplitude of the cardiac impedance-indicating component signal providing a possible indication of lung fluid accumulation.

FIG. 4B is a plot 402 illustrating a conceptual example of a signal curve 404 representing a generally decreasing amplitude over time (e.g., hours, days or weeks marked by separation 406) of the cardiac impedance-indicating component of a measured thoracic impedance-indicating signal. In this example, the cardiac impedance-indicating component signal has an amplitude of A at a first time and a decreased amplitude of B at a second time. In varying examples, the second time is hours, days or weeks later in time than the first time. As discussed above, this decreasing pulsation amplitude of the cardiac impedance-indicating component signal can indicate excess lung 204, 206 (FIG. 3A) fluid accumulation, such as pulmonary edema.

Figure 5:
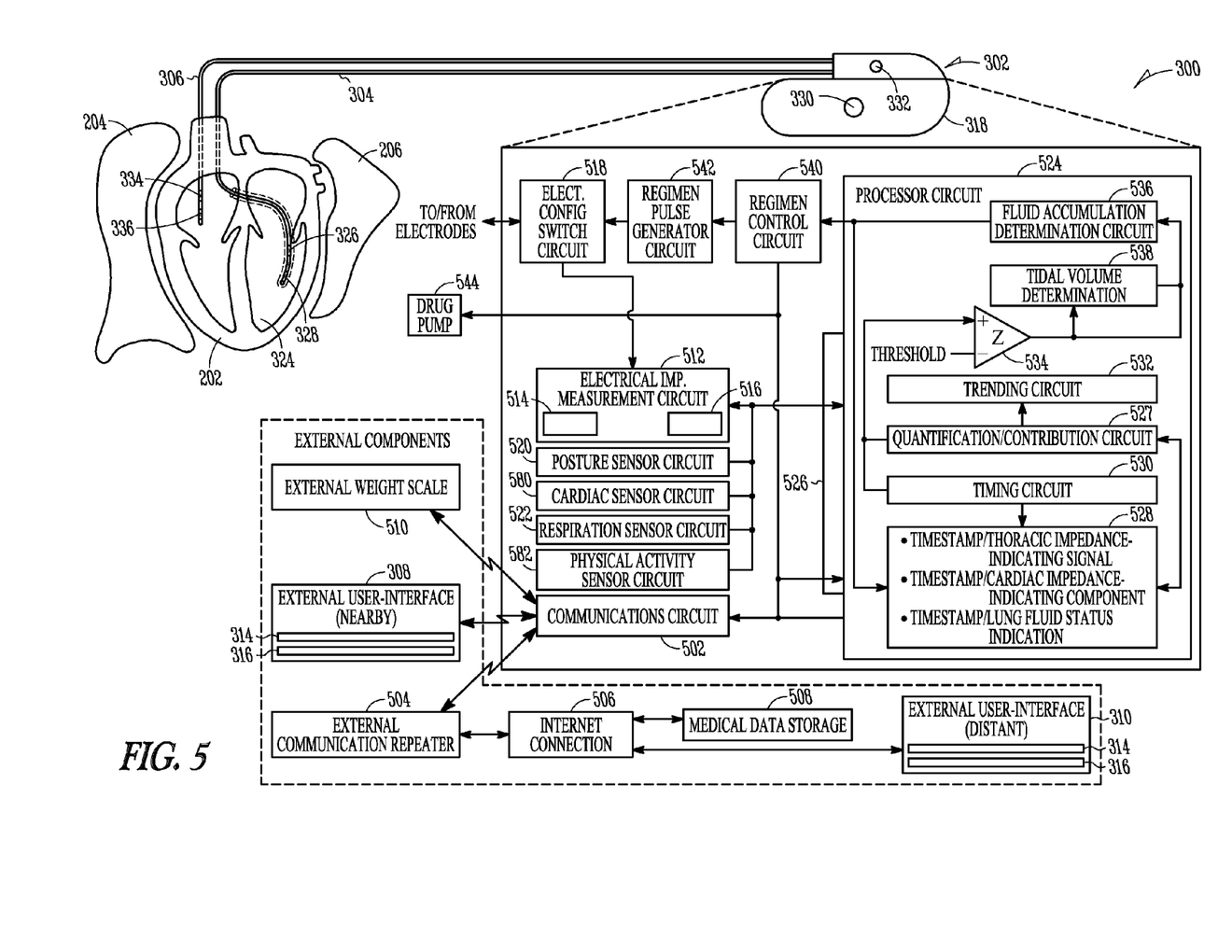
FIG. 5 is a block diagram illustrating one conceptual example of a system configured for monitoring excess fluid accumulation in a subject's lungs using information about the cardiac impedance-indicating component of a measured thoracic impedance-indicating signal.

FIG. 5 is a block diagram illustrating generally, by way of example, but not by way of limitation, a conceptual example of a system 300 configured for monitoring excess fluid accumulation in a subject's lungs 204, 206, such as by using information about the cardiac impedance-indicating component of a measured thoracic impedance-indicating signal. In this example, the system 300 includes a hermetically sealed IMD 302 coupled to a subject's heart 202 by one or more electrode-bearing intravascular leads, such as a left ventricular lead 304 having electrodes 326, 328 and a right atrial lead 306 having electrodes 334, 336, and one or more programmers or other external user-interface devices 308 (nearby), 310 (distant). In the example shown, the IMD 302 includes circuitry for measuring thoracic impedance at specified times for assessing lung fluid accumulation, and a communication circuit 502 for interfacing with external components.

The communication circuit 502 can be configured for wirelessly communicating with a communication circuit of the nearby external user-interface device 308. In certain examples, the communication circuit 502 is configured for wirelessly communicating with a communication circuit of a distant external user-interface device 310, such as by using a nearby external communication repeater 504. In one such example, the external communication repeater 504 is coupled to the distant external user-interface device 316 via an Internet or telephone connection 506. The Internet or telephone connection 506, in certain examples, allows the external communication repeater 504 to communicate with an electronic medical data storage 508. In a further example, the communication circuit 502 of the IMD 302 is communicatively coupled to a communication circuit of an external weight scale 510 or other external sensor. One example of a suitable external weight scale 510 is described in commonly-owned Belalcazar, U.S. patent application Ser. No. 11/419,120, entitled "MONITORING FLUID IN A SUBJECT USING A WEIGHT SCALE," which is incorporated herein by reference in its entirety, including its description of an external weight scale used to measure a voltage potential created by an injected energy.

The present system 300 monitors an amplitude or contribution of the cardiac impedance-indicating component of a thoracic impedance measurement, and in so doing, indirectly monitors a thoracic path travel by an injected electrical energy used in the thoracic impedance measurement, to provide an indication of fluid status within a lung. Thus, the IMD 302 includes an electrical impedance measurement circuit 512 that is electrically connected to the lead electrodes 326, 328, 334, 336 and a housing or header electrode 330, 332, respectively. The electrical impedance measurement circuit 512 includes an injected electrical energy generator circuit 514, a voltage measurement circuit 516, an analog-to-digital (A/D) converter (not shown), and a signal processor (not shown and which can be implemented elsewhere, such as with a processor circuit 524). The electrical energy generator circuit 514 is configured to generate and inject a current or other electrical energy between at least two electrodes, such as excitation electrodes. The voltage measurement circuit 516 is configured to measure a potential difference created by the injected energy between the same or different at least two electrodes, such as pick-up electrodes. The voltage measurement circuit 516 may optionally include a demodulator. In various examples, the electrodes used to inject the energy or to measure the resulting potential difference are selected by an electrode configuration switch circuit 518. The A/D converter is used to translate the analog information gathered by the electrical energy generator circuit 514 and the voltage measurement circuit 516 to a proportional digital number. Once so digitized, these values can be applied as inputs to the signal processor for calculating a thoracic impedance value by dividing the potential difference by the injected current (as specified by Ohm's law).

In the interest of normalized, stable measurement results or repeatability, thoracic impedance measurements, and thus cardiac impedance-indicating component measurements, may be taken at specified postures, activity levels, or at the same moment in one or both of a subject's cardiac or respiratory cycles. Thus, in this example, the IMD 302 can include a posture sensor circuit 520, a respiration sensor circuit 522, a cardiac sensor circuit 580, or a physical activity sensor circuit 582 therewithin or implanted nearby and communicatively coupled thereto. Additionally, information from the circuits can be used to adjust a relationship (e.g., via a state correction circuit associated with the processor circuit 524) between the measured thoracic impedance measurement(s) and the degree of edema or ensure certain impedance sampling parameters are met.

For instance, the posture sensor circuit 520 can be configured to produce a posture signal indicative of a posture of a subject. The posture signal can be used by the system 300 to trigger the electrical impedance measurement circuit 512 to measure a thoracic impedance-indicating signal at one or more specified posture positions or when a stable posture has been detected. Further, the posture signal can provide subject orientation information to the state correction circuit. This allows posture compensation to be included in the assessment of edema. Because organs and excess fluid in the thorax and lungs can shift with posture changes due to gravity, measured impedance may vary as a subject 301 (FIG. 3) assumes different positions. One or more of several types of posture sensors could be used, including one or any combination of a mercury switch, a tilt switch, a single axis accelerometer, a multi-axis accelerometer, or piezoelectric or other devices.

The respiration sensor circuit 522, such as a minute ventilation (MV) sensor, motion sensor, strain gauge on the diaphragm, or other activity sensor, can be configured to produce a respiration signal, which can indicate a moment of end-inspiration or end-expiration. The respiration signal can be used by the system 300 to trigger the electrical impedance measurement circuit 512 to measure a thoracic impedance-indicating signal, and thus the associated cardiac impedance-indicating component, at specified respiration moments, such as at one or a combination of end-inspiration or end-expiration, for sensitivity or reproducibility purposes. It is believed that the cardiac impedance-indicating component is most sensitive to change, though not the most reproducible, at end-expiration with stable tidal volumes at stable postures as less air is present within the subject's lungs 204, 206. It is further believed that measuring the cardiac impedance-indicating component at end-inspiration is the most stable and reproducible, but not the most sensitive due to more air being present with the subject's lungs 204, 206.

The IMD 302 can further include a timing 530 or other circuit, such as the cardiac sensor circuit 580 or the physical activity sensor circuit 582, so-as-to synchronize impedance sampling to a specified portion of the subject's cardiac cycle or activity state. In this way, the IMD 302 can save power by limiting the thoracic impedance measurements, and thus cardiac impedance-indicating component measurements, to fixed, triggered periods. Any of the sensors 520, 522, 580 or 582 can optionally be excluded from the IMD 302. During intervening intervals, such circuitry can be powered-down, or switched to more sporadic measurements, rather than performing continuous thoracic impedance measurements.

An implantable or external processor circuit 524 can include one or more inputs 526 to receive information about the measured thoracic impedance-indicating signal, the posture signal, the respiration signal, and any other information gathered or received by an external device or sensor. In various examples, the processor circuit 524 can include a quantification/contribution circuit 527 that is configured for determining one or both of an amplitude or contribution coefficient (to the total thoracic impedance measured) of the cardiac impedance-indicating component. The higher the magnitude of the amplitude or contribution coefficient, the more significantly the cardiac impedance-indicating component contributes to the total thoracic impedance measured.

In this example, an on-board memory 528 stores information about the thoracic impedance-indicating signal, the cardiac impedance-indicating component, or a lung fluid status indication provided by the processor circuit 524 along with a timestamp associated with such signals or indication. Additionally, in various examples, the on-board memory 528 can receive and store the programming of the IMD 302, which is used by the processor circuit 524 when implementing the necessary logic operations of the system 300. In one example, the timestamp is produced by the timing circuit 530 in communication with the memory 528.

In various examples, the processor circuit 524 further includes at least one evaluation circuit, such as a trending circuit 532, which is configured to trend over multiple cardiac or respiratory cycles information (e.g., amplitude or contribution to the overall thoracic impedance measurement) about the cardiac impedance-indicating component. In one example, the raw amplitude or contribution information of the cardiac impedance-indicating component or the trended information about the cardiac impedance-indicating component can be input to a comparator 534, which compares the data to a specified threshold that is also input to the comparator 534. If it is found that the input data exhibits a characteristic of present or impending lung fluid accumulation, such as an indication that the amplitude of the cardiac impedance-indicating component is decreasing due to a greater portion of the injected energy passing through the lung(s) 204, 206 rather than the heart 202 or is otherwise significant, the resulting comparison can be forwarded to a fluid accumulation determination circuit 536, which is configured to use such information to provide a lung fluid status indication, such as an indication of present or impending lung fluid accumulation. Optionally, an indication of a subject's tidal volume over multiple respiratory cycles provided by a tidal volume determination circuit 538 can be forwarded to the fluid accumulation determination circuit 536, such as for use in determining present or impending lung fluid accumulation.

In various examples, the system 300 includes a regimen control circuit 540 configured for initiating or adjusting a regimen (e.g., a therapy) to a subject 301 (FIG. 3A) at least in part by using information about at least one of the cardiac impedance-indicating component or the lung fluid status indication. In one example, such regimen includes electrical stimulation, such as cardiac pacing, resynchronization, cardioversion, or defibrillation stimulation, generated by a regimen pulse generator circuit 542 and delivered via one or more electrodes selected by the electrode configuration switch circuit 518. The one or more electrodes are selected individually or in combination to serve as an anode or a cathode in any unipolar, bipolar or multipolar configuration.

In another example, such regimen is provided elsewhere (e.g., communicated to the nearby external user-interface 308 or delivered via an implantable drug pump 544) and includes, for example, a drug dose, a diet regimen, or a fluid intake regimen. In one example, the drug dose can include a set of one or more drug regimen instructions communicated and displayed on the external user-interface 308, and more specifically the user-detectable indication 314. In certain examples, the set of drug regimen instructions includes a suggested daily intake schedule of one or more drugs, such as antiotension-converting enzyme (ACE) inhibitors, beta blockers, digitalis, diuretics, vasodilators, or the like. The drug dose can be automatically delivered per the suggested daily intake schedule via the implantable drug pump 544 or another drug dispensing device provided within the IMD 302 or implanted nearby and coupled thereto.

In a similar manner, the diet regimen and the fluid intake regimen can be communicated to the subject 301 via the user-detectable indication 314 of the external user-interface 308. In one example, the diet regimen can include a set of one or more dietary instructions to be followed by the subject 301, such as restriction of sodium to 2 grams or less per day and no more than one alcoholic drink per day. In another example, the fluid intake regimen can include a set of one or more fluid intake instructions to be followed by the subject 301, such as to avoid consuming an excess amount of fluid. FIG. 5 illustrates just one conceptualization of various circuits, devices, and interfaces of the system 300, which are implemented either in hardware or as one or more sequences of steps carried out on a microprocessor or other controller. Such circuits, devices, and interfaces are illustrated separately for conceptual clarity; however, it is to be understood that the various circuits, devices, and interfaces of FIG. 5 need not be separately embodied, but can be combined or otherwise implemented.

Figure 6:
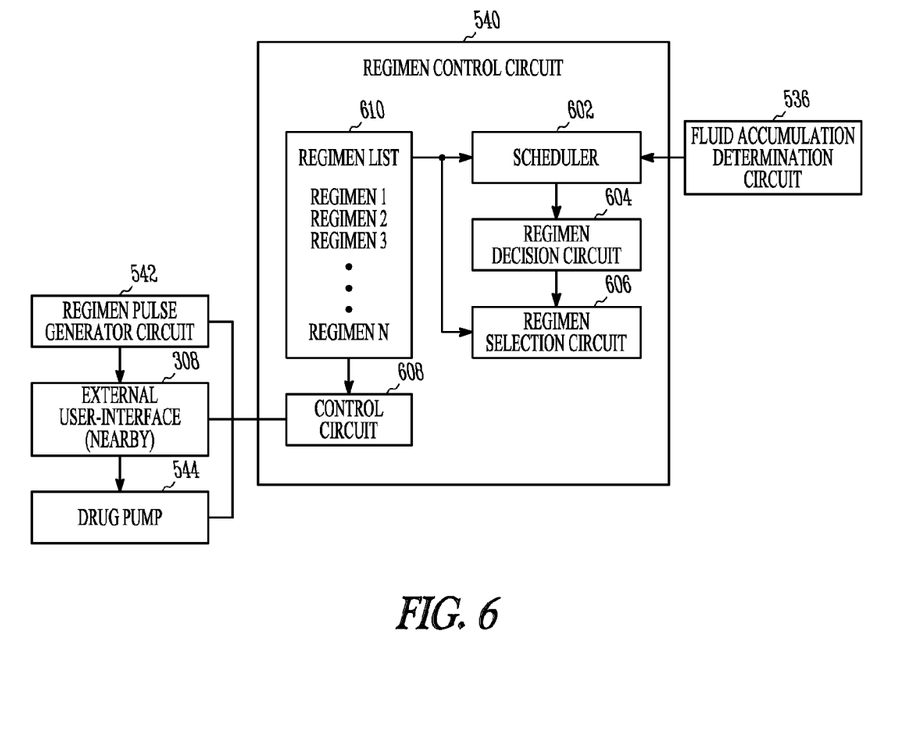
FIG. 6 is a block diagram illustrating one conceptual example of a regimen control circuit for use in the present fluid monitoring systems and methods.

FIG. 6 is a block diagram illustrating one conceptual example of a regimen control circuit 540, which can be used to trigger one or more regimens (e.g., therapies) to a subject 301 (FIG. 3A) in response to information about at least one of a cardiac component signal of a measured thoracic impedance signal or an indication of present or impending fluid accumulation. The regimen control circuit 540 can include an input that receives an indication of present or impending lung fluid accumulation output from a fluid accumulation determination circuit 536. In an example, a scheduler 602 schedules the indications of present or impending lung fluid accumulation. A regimen decision circuit 604 decides whether some form of regimen is warranted. If a regimen is deemed to be warranted, a regimen selection circuit 606 selects one or more appropriate regimens. A control circuit 608 adjusts the selected regimen via an output to one or more of a regimen pulse generator circuit 542, a nearby external user-interface 308, or a drug pump 544, for example.

The regimen control circuit 540 can include a regimen list 610, which can relate the regimens of the list 610 to the highest contributor(s) to the indication of present or impending lung fluid accumulation. In one example, the regimen list 610 includes all possible disease state preventive regimens or secondarily related regimens that the present system 300 (FIG. 5) can deliver or communicate to the subject 301 (FIG. 3A). The therapy list 610 can be programmed into an IMD 302 (FIG. 5) either in hardware, firmware, or software and stored in a memory 528 (FIG. 5). In another example, the regimen list 610 includes immediate, short-term, intermediate-term, or long-term fluid accumulation preventive therapies. Immediate fluid accumulation preventive therapies can include, by way of example, initiating or changing a drug dose administered to the subject via an implantable drug pump 544 or electrical stimulation administered to the subject 301 via the regimen pulse generator circuit 542. Short-term fluid accumulation preventive regimens can include, by way of example, administering a continuous positive air pressure ("CPAP") dose to the subject 301 or notifying a caregiver to initiate or change the subject's drug dose treatment program. Intermediate-term fluid accumulation preventive regimens can include, by way of example, adjusting the subject's 301 lifestyle such as his or her diet or fluid intake regimen. Finally, long-term fluid accumulation preventive regimens can include, by way of example, notifying the subject 301 or caregiver to alter the drug which takes longer to affect the subject (e.g., beta blockers, ACE inhibitors) or administering CRT to the subject 301.

Each member of the regimen list 610 can be associated with a corresponding time of action, which can include information about one or more of a time for the regimen to become effective or a time after which the regimen is no longer effective. In one example, only one member of the regimen list 610 is invoked at any particular time. In another example, combinations of different regimens are provided at substantially the same time. The various subcircuits in the regimen control circuit 540 are illustrated as such for conceptual purposes only; however, these subcircuits can alternatively be incorporated in the fluid accumulation determination circuit 536 or elsewhere, such as being implemented as a set of programmed instructions performed by a general purpose controller or other circuit.

Figure 7:
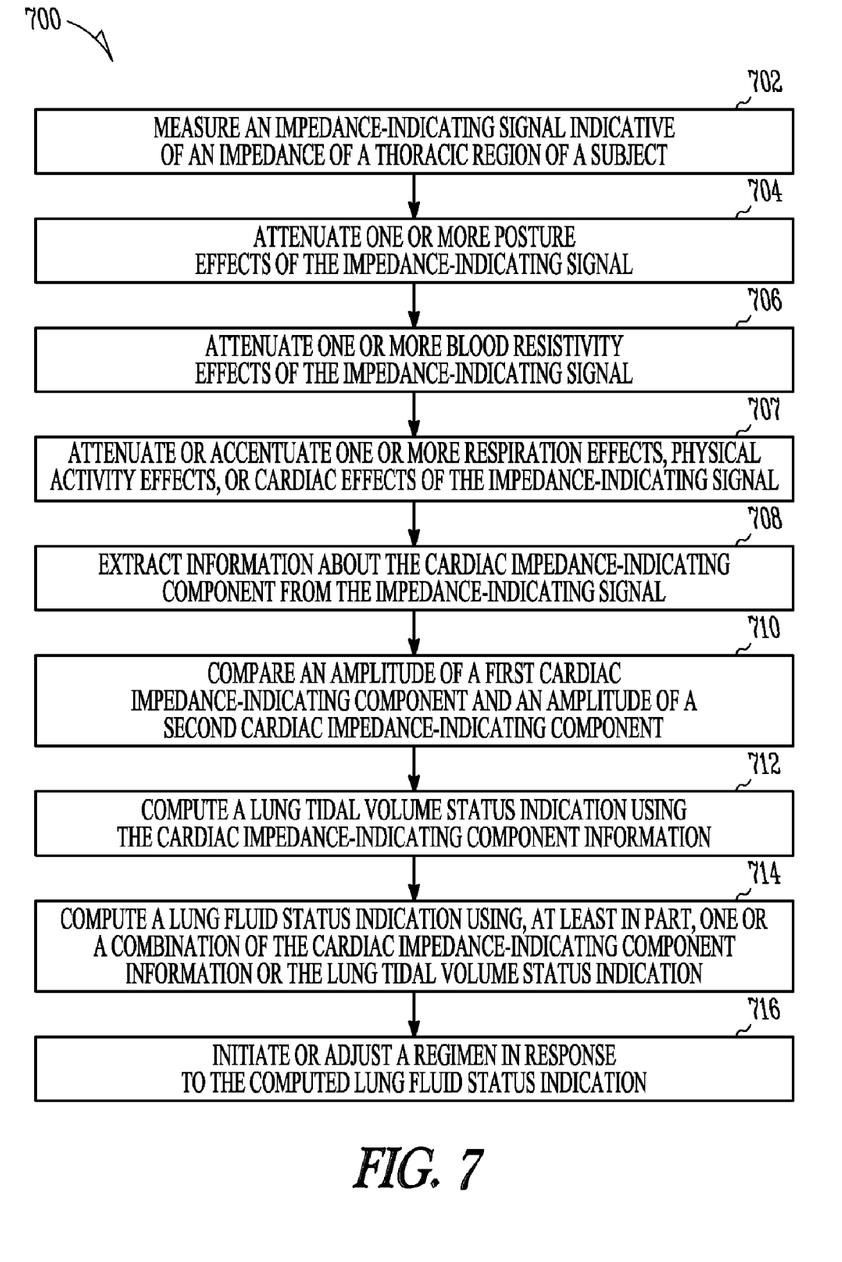
FIG. 7 is a block diagram illustrating one conceptual method of monitoring excess fluid accumulation in a subject's lungs using one or both of amplitude or contribution information about the cardiac impedance-indicating component of a measured thoracic impedance-indicating signal.

FIG. 7 is a block diagram illustrating a method 700 of monitoring excess fluid accumulation in a subject's lungs. At 702, an impedance-indicating signal indicative of an impedance of a thoracic region of a subject is measured between at least two electrodes. In one example, the impedance-indicating signal is measured by injecting sub-stimulation electrical energy, such as a current, between a distal electrode disposed on a left ventricular lead and one of a housing or a header electrode of an implantable medical device, and measuring a potential difference resulting from the injected energy between a proximal electrode disposed on the left ventricular lead and one of the housing or the header electrode. In another example, the impedance-indicating signal is measured at one or a combination of end-inspiration or end-expiration, which is detected by a respiration sensor circuit.

At 704, one or more posture effects of the impedance-indicating signal are attenuated. Because organs and excess fluid in the subject's thoracic region shifts with posture changes due to gravity, measured impedance can vary as the subject assumes different positions. For example, when the subject lies on his or her right side, fluid and tissues in the left lung may gravitate towards the mediastinum near electrodes disposed in the left ventricular coronary veins resulting in lower measured impedance. Thus, based on posture sensor information, the relationship between the impedance measured and the degree of edema may be adjusted to compensate for posture effects. Several types of postures sensors can be used, including mercury switches, DC-accelerometers, or other piezoelectric devices.

At 706, one or more blood resistivity effects of the impedance-indicating signal are attenuated. Blood resistivity changes as a function of hematocrit in the blood. The hematocrit (Ht) or packed cell volume (PCV) is the proportion of blood that is occupied by red blood cells. It is typically between 0.35 and 0.52, and is slightly higher, on average, in males than in females. For example, when the subject is dehydrated, there will be less fluid in the subject's blood. Therefore, the subject's hematocrit level will increase, that is, the subject's blood will include a higher percentage of other components, such as insulative red blood cells. This will increase the blood resistivity, which, in turn may affect the measured thoracic impedance even though it is not necessarily associated with the extravascular fluid accumulation of pulmonary edema. Accordingly, based on blood impedance measurement information, the relationship between the impedance measured and the degree of edema may be adjusted to compensate for blood resistivity effects as described in commonly-owned Stahmann et al., U.S. patent application Ser. No. 10/921,503, "THORACIC IMPEDANCE DETECTION WITH BLOOD RESISTIVITY COMPENSATION," which is incorporated herein by reference in its entirety, including its equations for representing a blood resistivity-compensated impedance-indicating signal.

At 707, one or more other state correction factors, such as respiratory effects, physical activity effects, or cardiac effects, of the impedance-indicating signal are attenuated or accentuated. For instance, information about the respiratory effects, physical activity effects, or cardiac effects can be attenuated to adjust the relationship between the measured impedance-indicating signal and a degree of edema. Alternatively, information about the one or more state correction factors, such as respiration, can be used to trigger an impedance measured to be in sync with one or a combination of end-inspiration or end-expiration.

At 708, information about the cardiac impedance-indicating component is extracted from the measured impedance-indicating signal. In various examples, the information about the cardiac impedance-indicating component includes one or both of an amplitude or contribution (to the total thoracic impedance measured) of the cardiac component. At 710, an amplitude of a first cardiac impedance-indicating component is compared to an amplitude of a second cardiac impedance-indicating component to provide a change over time (e.g., over multiple cardiac or respiratory cycles) of the cardiac impedance-indicating component, which can be used to compute a lung fluid status indication at 714.

At 712, a tidal volume of the subject is determined using, at least in part, the extracted information about the cardiac impedance-indicating component. Monitoring of respiration tidal volume is possible using information about the cardiac impedance-indicating component since air content causes the current diversion discussed above. Advantageously, no long time constants are required to implement such tidal volume monitoring.

At 714, a lung fluid status indication indicative of a level of lung fluid accumulation is determined using at least one of the cardiac impedance-indicating component information or the lung tidal volume status indication. In one example, the lung fluid status indication provides an indication of the presence or absence of pulmonary edema. An alert or alarm function, such as an acoustic signal emission, vibration, or low level pulse(s) recognizable by the subject, can be issued to indicate a need for regimen intervention upon a positive indication of excess lung fluid accumulation. Such an alert or alarm function can also be signaled by telemetry from the IMD to a remote programmer or other external user-interface for review by the subject's caregiver. At 716, a regimen is initiated or adjusted in response to the positive indication of excess lung fluid accumulation.

CONCLUSION

Chronic diseases, such as heart failure, can benefit from close medical management to reduce hospitalizations, morbidity, and mortality. Because such disease status evolves with time, frequent physician follow-up examinations are often necessary. The approach of periodic in-person follow-up is unsatisfactory for diseases like heart failure, in which acute, life-threatening exacerbations (e.g., heart failure decompensation and associated acute pulmonary edema) can develop between physician follow-up examinations. Pulmonary edema is a serious medical condition in which an excess amount of fluid accumulates in or around a subject's lungs. This condition can, and often does, result from heart failure. Pulmonary edema can require immediate care. While it can sometimes prove fatal, the outlook for subjects possessing pulmonary edema can be good upon early detection and prompt treatment.

Advantageously, the present systems and methods can provide for enhanced monitoring of excess fluid accumulation in a subject's thoracic region and thus, can provide a more timely or accurate detection of thoracic fluid accumulation than is currently available. Such detection is made possible by, among other things, generating a measured thoracic impedance-indicating signal and extracting from this signal information about the cardiac impedance-indicating component, such as the component's amplitude or contribution (to the total measured thoracic impedance) trend over multiple cardiac cycles. Once extracted, this cardiac impedance-indicating component information can be used to determine an indication of present or impending lung fluid accumulation.

Unlike previous fluid monitoring systems and methods, determining the indication of present or impending lung fluid accumulation using the present systems and methods does not depend on a highly-filtered, low frequency DC or near-DC component of a thoracic impedance-indicating signal. Rather, the indication of present or impending lung fluid accumulation can be found, at least in some examples, through the use of a thoracic impedance-indicating signal including higher frequency AC components thereby providing simpler monitoring, which may be less costly to implement.

CLOSING NOTES

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "implantable medical device" or simply "IMD" is used to include, but is not limited to, implantable cardiac rhythm management (CRM) systems such as pacemakers, cardioverters/defibrillators, pacemakers/defibrillators, biventricular or other multi-site resynchronization or coordination devices such as cardiac resynchronization therapy (CRT) device, subject monitoring systems, neural modulation systems, or drug delivery systems. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine-implemented or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more features thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. In addition, while the majority of this patent document discusses the monitoring of fluid in a thoracic region of a subject, the present systems and methods can be used in ways similar to those discussed herein to monitor fluid accumulation in other regions of a subject's body. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. A system comprising:
    an implantable medical device including an electrical impedance measurement circuit configured for injecting electrical energy between two or more electrodes and for concurrently measuring a potential difference created thereby in a thoracic region of a subject between the same or different two or more electrodes; and
    an implantable or external processor circuit including an input to receive the information about the injected electrical energy and the measured potential difference, the processor circuit configured to compute an impedance-indicating signal using the information about the electrical energy and the potential difference, the processor circuit further configured to extract an alternating current (AC) cardiac impedance-indicating component of the impedance-indicating signal including attenuating a respiration-indicating component of the impedance-indicating signal, then to extract AC amplitude information from the extracted AC cardiac impedance-indicating component, and to determine, using the extracted AC amplitude information, an AC amplitude change over time of the extracted AC cardiac impedance-indicating component of the impedance-indicating signal to provide a lung fluid status indication.

2. The system of claim 1, comprising a comparator circuit configured to compare an amplitude of a first cardiac impedance-indicating component to an amplitude of a second cardiac impedance-indicating component; and
wherein the processor circuit is configured to use information about the comparison to provide the lung fluid status indication.

3. The system of claim 1, comprising a comparator circuit configured to compare the amplitude change over time of the cardiac impedance-indicating component to a specified threshold; and
wherein the processor circuit is configured to use information about the comparison to provide the lung fluid status indication.

4. The system of claim 1, comprising a contribution circuit configured to compute a contribution coefficient of the cardiac impedance-indicating component to the impedance-indicating signal; and
wherein the processor circuit is configured to use information about the contribution coefficient to provide the lung fluid status indication.

5. The system of claim 1, comprising a memory circuit configured to store information about the amplitude change over time of the cardiac impedance-indicating component, the time association with the amplitude change exceeding a respiration cycle length time.

6. The system of claim 1, comprising a regimen control circuit configured to initiate or adjust a regimen provided to the subject using, at least in part, information about at least one of the amplitude change over time of the cardiac impedance-indicating component or the lung fluid status indication.

7. The system of claim 1, comprising an external user-interface device communicatively coupled to the implantable medical device and including a user-detectable indication of at least one of the change over time of the cardiac impedance-indicating component or the lung fluid status indication.

8. The system of claim 7, wherein the external user-interface device includes a user input device configured to receive programming information from a user and to communicate the programming information to the implantable medical device.

9. The system of claim 1, comprising a respiration sensor configured to produce a respiration signal indicative of a moment of one or a combination of end-inspiration or end-expiration; and
wherein the electrical impedance measurement circuit is configured to measure the impedance-indicating signal at the respiration signal.

10. The system of claim 1, comprising a posture sensor circuit configured to produce a posture signal indicative of a posture of a subject; and
wherein the electrical impedance measurement circuit is configured to measure the impedance-indicating signal at a specified posture signal.

11. A method comprising:
measuring an impedance-indicating signal indicative of an impedance of a thoracic region of a subject between at least two electrodes;
using a processor circuit to extract an AC cardiac impedance-indicating component of the impedance-indicating signal, including attenuating a respiration-indicating component of the impedance-indicating signal;
using the processor circuit to extract AC amplitude information from the extracted AC cardiac impedance-indicating component from the impedance-indicating signal; and
using the processor circuit to compute a lung fluid status indication using, at least in part, the extracted AC amplitude information about the cardiac impedance-indicating component.

12. The method of claim 11, wherein measuring the impedance-indicating signal includes:
injecting electrical energy between a first and a second electrode implanted in the thoracic region of the subject; and
measuring a potential difference between a third and a fourth electrode implanted in the thoracic region of the subject, the potential difference resulting from the electrical energy injected between the first and second electrodes.

13. The method of claim 12, comprising determining an amount of the injected electrical energy which traverses a heart of the subject using the extracted amplitude information about the cardiac impedance-indicating component; and
wherein computing the lung fluid status indication includes using the amount of the injected electrical energy which traverses the heart.

14. The method of claim 12, comprising determining an approximate amount of the injected electrical energy which traverses a lung of the subject using the extracted amplitude information about the cardiac impedance-indicating component; and
wherein computing the lung fluid status indication includes using the amount of the injected electrical energy which traverses the lung.

15. The method of claim 12, wherein injecting the electrical energy includes injecting an electrical current between an electrode disposed on a left ventricular lead and one of a housing or a header electrode of an implantable medical device; and
wherein measuring the potential difference includes detecting a voltage potential between an electrode disposed on the left ventricular lead and one of the housing or the header electrode.

16. The method of claim 11, comprising comparing an amplitude of a first cardiac impedance-indicating component and an amplitude of a second cardiac impedance-indicating component, including determining an amplitude change over a period of time exceeding a respiration cycle length time of the cardiac impedance-indicating component.

17. The method of claim 16, comprising comparing the change over the period of time of the cardiac impedance-indicating component to a specified threshold.

18. The method of claim 11, comprising positioning at least one of the two or more electrodes near the interface between a heart and a lung of the subject.

19. The method of claim 11, comprising attenuating one or a combination of a posture effect, a blood resistivity effect, a physical activity state effect, or a cardiac effect from at least one of the impedance-indicating signal or the cardiac impedance-indicating component.

20. The method of claim 11, comprising initiating or adjusting a regimen in response to the computed lung fluid status indication.

21. The method of claim 11, comprising measuring the impedance-indicating signal at a first injection electrical energy frequency and measuring the impedance-indicating signal at a second injection electrical energy frequency different from the first injection electrical energy frequency; and
determining a level of confidence in the computed lung fluid status indication using cardiac impedance-indicating component information extracted from the impedance-indicating signals measured at the first and second injection frequencies.

22. The method of claim 11, comprising computing a lung tidal volume status indication using, at least in part, the extracted amplitude information about the cardiac impedance-indicating component.

23. The method of claim 11, wherein measuring the impedance-indicating signal includes measuring the impedance at one or a combination of end-inspiration or end-expiration.

24. The method of claim 11, wherein extracting the amplitude information includes calculating a ratio of the cardiac impedance-indicating component to the impedance-indicating signal.

25. The method of claim 11, wherein computing the lung fluid status indication includes detecting a decrease in the amplitude of the cardiac impedance-indicating component over time.

26. The method of claim 11, wherein computing the lung fluid status indication includes determining the presence or absence of pulmonary edema.

* * * * *